(12) United States Patent
Gonzales (10) Patent No.: US 7,387,638 B2
(45) Date of Patent: Jun. 17, 2008

(54) SYSTEM AND METHOD USING THE RECTAL MUCOSAL MEMBRANE FOR INDUCING HYPOTHERMIA AND WARMING

(75) Inventor: Gilbert R. Gonzales, New York, NY (US)

(73) Assignee: Serene Medical, Inc., New York, NY (US)

( * ) Notice: Subject to any disclaimer, the term of this patent is extended or adjusted under 35 U.S.C. 154(b) by 457 days.

(21) Appl. No.: 11/224,363

(22) Filed: Sep. 12, 2005

(65) Prior Publication Data

US 2006/0009824 A1    Jan. 12, 2006

Related U.S. Application Data

(63) Continuation of application No. 10/224,023, filed on Aug. 20, 2002, now abandoned.

(51) Int. Cl.
*A61F 7/00* (2006.01)
(52) U.S. Cl. .......................... 607/96; 607/105; 606/21; 606/27
(58) Field of Classification Search .................. 607/88, 607/96, 104–107; 606/13–15, 20–31; 604/48, 604/131
See application file for complete search history.

(56) References Cited

U.S. PATENT DOCUMENTS

| 3,125,096 | A |   | 3/1964 | Antiles et al. |
|-----------|---|---|--------|----------------|
| 3,683,655 | A | * | 8/1972 | White et al. .................. 601/44 |
| 3,976,056 | A | * | 8/1976 | Brawn ......................... 601/152 |
| 4,758,562 | A |   | 7/1988 | Adler et al. |
| 4,842,583 | A |   | 6/1989 | Majlessi |
| 4,932,958 | A |   | 6/1990 | Reddy et al. |
| 4,946,449 | A |   | 8/1990 | Davis |
| 5,002,558 | A |   | 3/1991 | Klein et al. |
| 5,007,437 | A | * | 4/1991 | Sterzer ....................... 607/138 |
| 5,370,675 | A |   | 12/1994 | Edwards et al. |
| 5,474,533 | A |   | 12/1995 | Ward et al. |

(Continued)

FOREIGN PATENT DOCUMENTS

DE        3842396        6/1990

(Continued)

OTHER PUBLICATIONS

International Search Report, mailed Jun. 14, 2004.

*Primary Examiner*—Ahmed M Farah
(74) *Attorney, Agent, or Firm*—Wood, Herron & Evans, L.L.P.

(57) ABSTRACT

A system and method for cooling and warming the central nervous system of a patient comprises a delivery tube with one of the ends couplable to a supply of fluid. A head structure is coupled to the other end of the delivery tube and cooling or warming fluid is directed through the tube to the head structure. The head structure is configured to be placed within the rectal cavity of a patient such that either a contact surface on the head structure or the fluid itself directly contacts a portion of the rectal mucosal membrane. A means for reversing the vertebral venous flow of blood through Batson's plexus supplies cooled or warmed blood directly to the vertebral structures. Unique methods of utilizing the system to selectively cool and warm the central nervous system structures of a patient are set forth herein.

18 Claims, 7 Drawing Sheets

U.S. PATENT DOCUMENTS

| | | | |
|---|---|---|---|
| 5,486,204 A | | 1/1996 | Clifton |
| 5,496,271 A | | 3/1996 | Burton et al. |
| 5,716,386 A | * | 2/1998 | Ward et al. .................. 607/106 |
| 5,755,756 A | | 5/1998 | Freedman, Jr. et al. |
| 5,800,485 A | | 9/1998 | Trop et al. |
| 5,817,147 A | | 10/1998 | Wolf |
| 5,830,186 A | | 11/1998 | Gonzales et al. |
| 5,846,216 A | * | 12/1998 | Gonzales et al. .............. 604/2 |
| 5,957,963 A | | 9/1999 | Dobak, III |
| 5,976,079 A | * | 11/1999 | Volz et al. .................. 600/209 |
| 6,009,351 A | * | 12/1999 | Flachman ................... 607/101 |
| 6,077,257 A | | 6/2000 | Edwards et al. |
| 6,090,132 A | | 7/2000 | Fox |
| 6,126,684 A | | 10/2000 | Gobin et al. |
| 6,149,624 A | | 11/2000 | McShane |
| 6,156,057 A | | 12/2000 | Fox |
| 6,231,595 B1 | | 5/2001 | Dobak, III |
| 6,235,048 B1 | | 5/2001 | Dobak, III |
| 6,248,126 B1 | | 6/2001 | Lesser et al. |
| 7,243,655 B2 | * | 7/2007 | Gonzales .................... 128/898 |
| 2002/0004675 A1 | | 1/2002 | Lasheras |
| 2002/0068877 A1 | | 6/2002 | Abramovitch et al. |
| 2002/0151943 A1 | | 10/2002 | Balding |

FOREIGN PATENT DOCUMENTS

| | | |
|---|---|---|
| WO | WO 9529643 | 11/1995 |

* cited by examiner

SYSTEM AND METHOD USING THE RECTAL MUCOSAL MEMBRANE FOR INDUCING HYPOTHERMIA AND WARMING

CROSS-REFERENCE TO RELATED APPLICATION

This application is a continuation of U.S. patent application Ser. No. 10/224,023, entitled "System and Method Using the Rectal Mucosal Membrane for Inducing Hypothermia and Warming," filed on Aug. 20, 2002 now abandoned, the disclosure of which is incorporated herein by reference in its entirety.

FIELD OF THE INVENTION

The present invention relates generally to a system and method for cooling and warming the body and specifically relates to a system and method for selectively inducing hypothermia or warming in the central nervous system.

BACKGROUND OF THE INVENTION

Hypothermia, which is the condition of lowered normal body temperature in a warm-blooded animal, has been used therapeutically for the treatment of human brain injury, spinal cord injury, and spinal cord ischemia for many years. Therapeutic hypothermia is used as a neural protectant in situations where there is central nervous system ischemia, trauma, or hypoxia. Such situations can occur from stroke, global ischemia, accidental trauma, or may be induced during surgery. The induction of therapeutic hypothermia followed by rewarming is now an integral part of modern surgery. In fact, many surgical procedures currently performed are successfully accomplished with the aid of hypothermia. Hypothermia as a medical therapy is recognized as a method of preserving brain tissue in the setting of focal and global ischemia.

Normal core temperature for humans is in the range of 36-38° C. Medical and surgical hypothermic therapy is considered "mild hypothermia" when the core temperature is cooled to approximately 32-35° C., and "deep hypothermia" when the core temperature is reduced below 32° C. Hypothermia has been shown in animal models to reduce the permeability of the blood brain barrier. It also causes a reduction in metabolic activity, along with decreased cerebral demand for glucose and oxygen. Other effects of hypothermia on the brain and spinal cord include decreased rates of high-energy phosphate depletion, decreased lactate accumulation, reduced biosynthesis, and decreased release and uptake of some neurotransmitters. Hypothermia also lowers intracranial pressure and can inhibit brain edema. Individual organ hypothermia, such as that used on transplanted organs, is also used to preserve organs other than the central nervous system.

Known techniques for inducing hypothermia involve both surface cooling and internal cooling, sometimes in conjunction with drugs that disable homeostatic responses. For example, some present methods for inducing hypothermia by surface cooling include externally applied cold packs, whole body ice, ice blankets, immersion in ice water, and chilled forced air refrigeration. Some internal cooling techniques include methods such as infusion of cold saline into veins, arteries, and/or into the peritoneum, and direct extracorporeal cooling.

Surface techniques for achieving and maintaining central nervous system hypothermia are generally unsatisfactory for a number of reasons. First, the organ that is generally the focus of cooling, the central nervous system, is actually cooled last with such techniques. Also, the time to cool the central nervous system can be in the order of four hours or greater. Further, the inertia produced by a steady drop in temperature can produce an "overshoot" condition in which organ damage from excessive hypothermia can occur. Additionally, surface cooling, especially for deep hypothermia, often requires supplemental internal cooling and pharmacological assistance. Cooling by cold blankets and dressings is also often uncomfortable and induces shivering in the patient. Furthermore, there is a risk of body surface injury, and the need to anesthetize for deep hypothermia is often required. Similar drawbacks occur in warming or re-warming the body, such as re-warming a patient after hypothermia.

Internal cooling, on the other hand, is an invasive process which is associated with other problems, including infection, thrombosis, arrhythmia, and cardiac ischemia. Another problem is that the entire body is necessarily cooled in situations where only the central nervous system should be cooled. Because there are such problems associated with current methods of inducing hypothermia, a non-invasive cooling system and technique that is focused on the target organ, most notably the central nervous system, would be desirable. It is also desirable to have a non-invasive system for warming the body selectively.

Therefore, it is an object of the invention to provide targeted central nervous system cooling and warming. It is also an objective of the invention to provide a hypothermia/warming system and technique that minimizes or avoids an overshoot cooling or warming of the body. It is another objective of the invention to cool/warm the central nervous system in a non-invasive manner. It is further an objective of the invention to develop a hypothermia/warming system and technique, which can work concurrently and synergistically with existing cooling/warming systems.

SUMMARY OF THE INVENTION

The above-discussed objectives are addressed in the present invention, which comprises a system and method for selectively cooling/warming the central nervous system in a patient, as well as contribute to systemic cooling/warming. In one embodiment, the system includes cooling/warming fluid capable of transferring body heat or caloric energy, a head structure configured to receive the fluid, and a delivery tube to deliver the fluid to and from the head structure. The head structure is placed in the rectal cavity of a patient to cool/warm blood proximate the rectal cavity. The flow of blood cooled or warmed by the system is then reversed and delivered to the central nervous system through the vertebral venous plexus, or Batson's plexus.

Rectal mucosal membrane cooling/warming in conjunction with the reversal of blood flow through Batson's plexus provides direct cooling/warming of the spinal structures and other central nervous system areas. Reversal of flow in Batson's plexus refers to the physical phenomenon of reversing the flow of blood through the veins of the vertebral structures when intraabdominal pressure is applied. Normally, the vertebral venous plexus in the pelvis, sacrum and lumbar spine assist in carrying venous blood from the meningorrhachidian veins of the vertebral structures, including the spinal cord, to the sacrum, the sacral plexus, the iliac veins and ultimately to the inferior vena cava and to the heart. However, the vertebral venous plexus or Batson's plexus is valveless, so blood is free to flow in either direction. The Batson effect occurs upon increased intraabdominal pressure, which causes reversal of pelvic and lumbar venous flow. Venous blood then flows from the inferior vena cava and sacral venous plexus into the meningorrhachidian blood vessels. In short, normal blood flow occurs from the spinal column toward the heart, but under Batson's described effect, blood flow can occur in the opposite direction, providing blood flow back to the spinal structures.

By using Batson's plexus reverse blood flow by increased intraabdominal pressure in conjunction with cooling/warming of the blood draining the rectal mucosal membranes, internal cooling/warming is more efficiently and effectively accomplished at the spinal cord and brain, such as to induce hypothermia and recover from the hypothermia without the drawbacks of external or invasive techniques. In one embodiment of the invention, the head structure of the system is placed or positioned within the outermost two-thirds of the rectal cavity, commonly known as the ampulla. Caloric energy is transferred between the rectal mucosal membrane and the head structure and fluid, thereby cooling or warming, respectively, the blood draining the ampulla. While this is done, the direction of the vertebral venous blood flow is reversed so as to selectively direct the cooled or warmed blood retrograde through Batson's plexus and into the spinal structures, and with prolonged reversal to cranial structures.

The vertebral venous blood flow is preferably reversed by applying intraabdominal pressure to the patient's body. This is accomplished through a number of ways, such as by using an abdominal restraint or binder or lumbar support. As the blood flow in the vertebral venous plexus is reversed, the cooled or warmed blood is delivered from the rectal and sacral veins directly to the vertebral bones, the epidural and intrathecal space, and the spinal cord. By maintaining the increase in the intraabdominal pressure long enough, cranial structures will also be cooled by the venous blood flow.

In one aspect of the invention, the supply of fluid is delivered into a bulb through a delivery tube, such as through an IV drip bag or through a pump apparatus. The delivery tube preferably is bilumenal, having at least one inflow and one outflow lumen so that fluid can be circulated into and out of the bulb. The inflow lumen delivers the fluid directly to the bulb and the outflow lumen removes the fluid from the bulb. In one embodiment, the delivery tube is flexible and extends in length such that the fluid supply is generally remote from the patient.

The system may generally have several different embodiments, such as a "dry" system in which fluid remains at all times within the head structure, and a "wet" system in which fluid is able to exit the head structure to make direct contact with the rectal mucosal membrane. In the various embodiments, the head structure may take a variety of different forms, such as a single bulb, a flexible, expandable bag, a tandem configuration having a proximal bulb and a distal bulb, a helix, or any other suitable form for the wet or dry embodiments.

In the "dry" embodiment of the invention, the bulb has a contact surface, which is operable to transfer caloric energy or heat between the rectal mucosal membrane and the fluid. The fluid generally does not leave the bulb. The contact surface of the "dry" embodiment of the bulb has a large surface area that is able to make contact with a large amount of the rectal mucosal membrane. The head structure bulb preferably conforms to the shape of the rectal cavity after insertion into the rectum so that the contact surface can make extended contact with the rectal mucosal membrane.

In the "wet" embodiment of the invention, the contact surface of the bulb has a plurality of apertures therethrough. The fluid is directed through the apertures and out of the bulb, directly contacts the rectal mucosal membrane to cool or warm it, and then is drawn back through the apertures and into the bulb. The fluid is then directed out of the rectal cavity through the outflow lumen of the delivery tube.

The head structure can come in a variety of shapes and configurations. In one embodiment, the head structure is in a compressed form before insertion into the rectal cavity, and is thereafter able to expand once inside the rectal cavity. This allows for ease of insertion with minimal discomfort to the patient, while permitting maximal contact with the rectal mucosal membrane after insertion. In one embodiment, the head structure, now inside the rectal cavity, is able to further enlarge in size in direct relation to the delivery flow rate of the fluid from the delivery tube. In this embodiment, the head structure can be a flexible elongated bag that expands and enlarges in size as the fluid is delivered. In such an embodiment, the fluid is preferably delivered by a pump apparatus.

In another embodiment, the bulb does not significantly change shape or size after its initial expansion inside the rectal cavity. As the fluid circulates therethrough, its size and shape remain generally constant regardless of the flow rate of the fluid.

In yet another embodiment of the system, the cooling/warming head structure is configured having a proximal bulb and a distal bulb positioned in tandem to each other. The proximal end of rectal cavity is defined herein for illustrative purposes, as being the end proximal to the anal outlet. The distal end or area is then distal to the anal outlet. In one such tandem bulb configuration of the head structure, the proximal bulb (closest to the anal outlet) receives cooling fluid while the distal bulb (deeper into the rectum or colon; further away from the anal outlet) remains warm or non-cooled. The proximal bulb is positioned in the portion of the rectal cavity, which is drained by the inferior and middle rectal veins such that the outermost two-thirds of the rectum, or ampulla, will be selectively cooled or warmed. The inferior and middle rectal veins directly supply the spinal cord and the central nervous system structures when intraabdominal pressure is applied to reverse the blood flow through Batson's plexus. The warm (noncooled) distal bulb can be positioned in the innermost one-third of the rectum to prevent cooling of that portion of the rectal mucosal membrane drained by the superior rectal vein. The superior rectal vein does not participate in Batson's plexus reversal of blood flow. Thus, the warm or non-cooled bulb is able to prevent portions of the body not related to the vertebral structures and/or the central nervous system from being actively cooled. In this manner, with the proximal bulb actively cooling or warming the spine and central nervous system structures and the distal bulb acting to keep other structures from being actively cooled or warmed, selective cooling or warming of the central nervous system can be accomplished. As discussed herein, the bulb which is generally not participating in the active cooling or warming may be maintained at a temperature that does not significantly affect the body or which prevents the cooling/warming of the other bulb from significantly affecting portions of the body.

The invention can be used to induce hypothermia and can be used to rewarm the patient after hypothermia is no longer required, or might be used to warm an individual with hypothermia induced by environmental exposure or other causes. The wet or dry systems would deliver a warming fluid without cold fluid delivery.

One wet embodiment of a tandem bulb configuration of the head structure allows fluid out through the apertures in order to bathe the rectal mucosal membrane. In such an embodiment, fluid is delivered to the proximal bulb and exits the proximal bulb through apertures to bathe the rectal mucosal membrane. The fluid is thereafter retrieved through apertures of the distal bulb and is then delivered to the outflow lumen of the delivery tube and out of the patient.

In all embodiments of the invention the system provides direct and precise cooling or warming of the spinal cord and other central nervous system structures without the drawbacks of the prior art. Various advantages and objectives of the present invention will become more readily apparent below from the brief description of the drawings and the detailed description of the invention.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
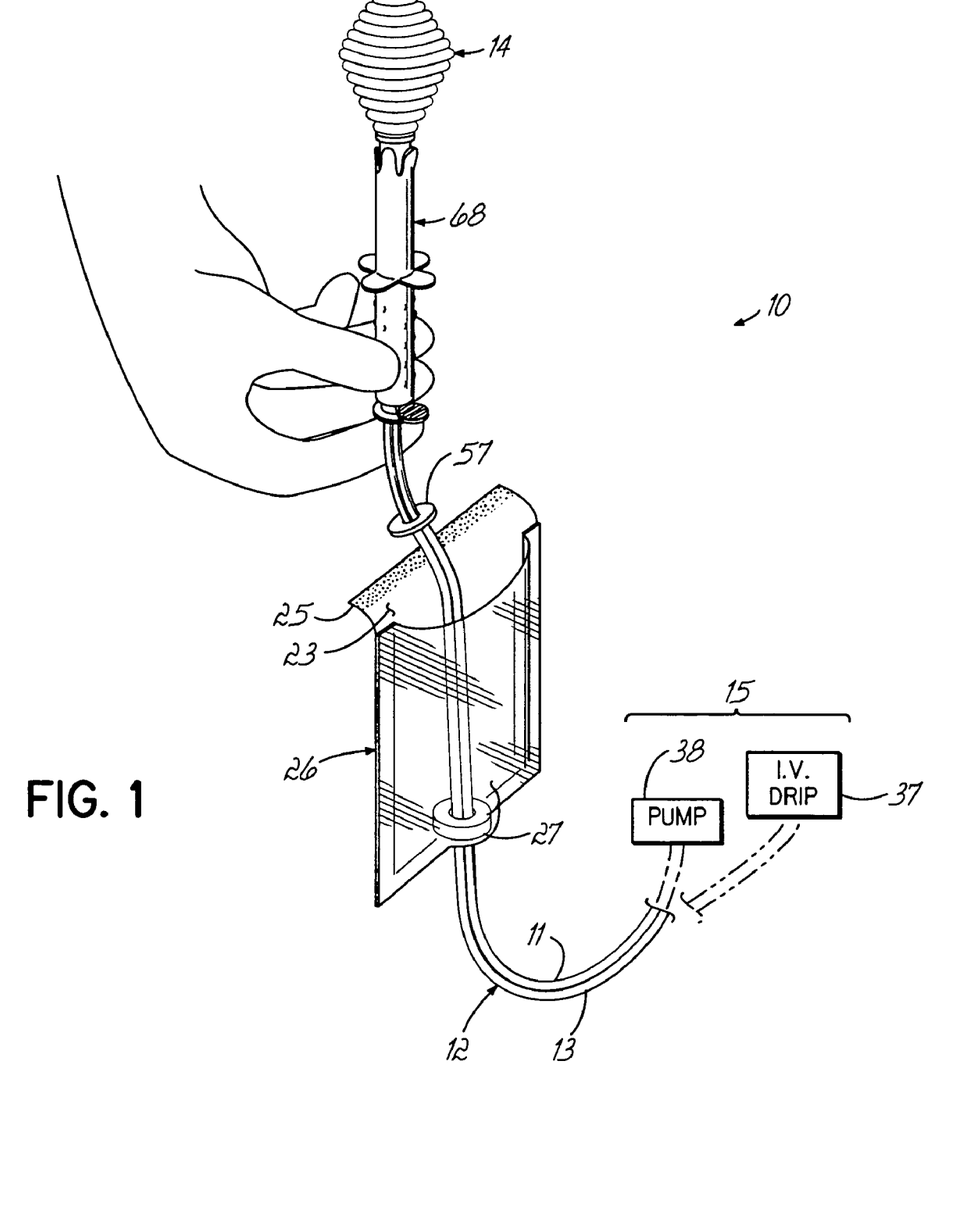
FIG. 1 is a schematic view of an embodiment of the system of the invention.

FIG. 1 is a schematic view of one embodiment of the cooling system 10 of the present invention. The system will be described in one embodiment herein for providing cooling and hypothermia. However, in accordance with another aspect, the system may be used for warming to counteract the induced hypothermia or to counteract other hypothermia or cooling conditions such as those associated with exposure to environmental conditions. The system 10 includes a delivery tube or tubes 12 which are coupled to a supply 15 of fluid to be dispensed therethrough. The supply 15 may include, for example, an I.V. drip bag 37 or a pump 38, for example. The delivery tube 12 is coupled to a cooling/warming head or head structure 14 that receives fluid delivered thereto by the delivery tube 12. The delivery tube 12 in one embodiment is bilumenal, having an inflow lumen 11 and an outflow lumen 13, thereby allowing the cooling fluid to be circulated into and out of the head structure 14. In several embodiments, the head structure 14 is in the shape of a bulb or multiple bulbs, but it may take other forms as well. For example, the head structure might be a helix as discussed below, an expandable bag, or may have a stellate cross-section such as that shown in U.S. Pat. Nos. 5,830,186 and 5,846,216.

As illustrated in FIG. 1, the end of the delivery tube 12 opposite the head structure 14 can be coupled to an I.V. drip bag 37 for continuously dispensing the fluid at a controlled drip rate into tube 12. Alternatively, the tube 12 might be connected to a pump device 38 for pumping the fluid into and out of the head structure 14 via the delivery tube 12 at a predetermined flow rate. When an I.V. is utilized, a vacuum pump or other structure (not shown) might be utilized with a "dry" embodiment of the invention to provide a proper flow through of fluid. The delivery tube 12 may be made of PVC material or of a suitable biodegradable material for more environmentally safe disposal, and preferably is flexible and extends in length such that the cooling fluid supply is generally remote from the patient.

As discussed further below, the head structure 14 is operable either to directly contact the rectal mucosal membrane for heat or caloric energy transfer between the rectal mucosal membrane and the fluid which remains inside the head structure (the "dry" embodiments of FIGS. 1 through 4); or to direct the fluid into and out of the head structure through apertures such that the fluid directly contacts the rectal mucosal membrane (the "wet" embodiments of FIGS. 5 and 7).

The fluid can be made up of any fluid that is able to be cooled or warmed. That is, any fluid that can absorb or disperse heat and attract or output caloric energy may be used in the invention. It is preferable, of course, that non-toxic fluids be used. Therefore, saline or water are two possible fluids for the invention. Concerning the "wet" embodiment of the invention, in which the fluid leaves the head structure through apertures to make contact with the rectal mucosal membranes, the fluid may have several additional characteristics that are advantageous. In one embodiment, the fluid is generally not absorbable into the bloodstream of the patient, thus assuring that the patient does not develop problems associated with increased fluid load or electrolyte imbalance. In another embodiment, the fluid may be at least partially absorbable into the bloodstream of the patient. In still another embodiment, the fluid may include an absorbable vasodilator medication that can act to increase the venous blood flow to the rectal mucosal membranes, thereby increasing the amount of blood that is actively cooled or warmed by the system. Vasodilation of the veins that drain the rectal mucosal membranes is advantageous because, when intraabdominal pressure is applied to reverse the venous blood flow through Batson's plexus, more cool or warm blood is available to bathe the central nervous system structures.

In accordance with another aspect of the present invention, a vasodilator may also be utilized in the "dry" versions of the invention. For example, as discussed further herein below, the head structure may be configured for dispensing a substance, such as a vasodilator, proximate and outside the "dry" head structure for enhancing the operation of the system.

Figure 2:
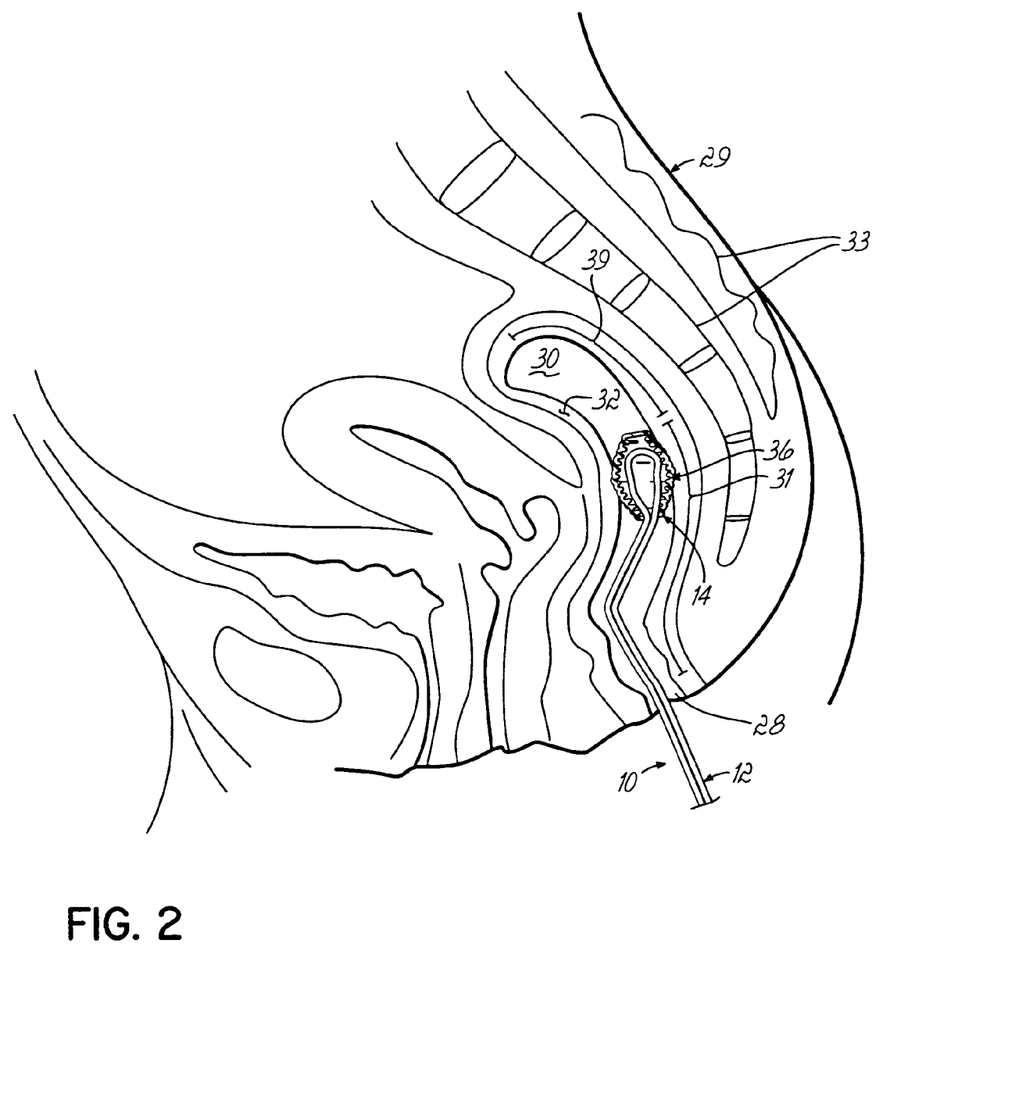
FIG. 2 is a side view, in partial cross-section, of a patient body illustrating one embodiment of the system used within the rectal cavity of the body.
Figure 3A:
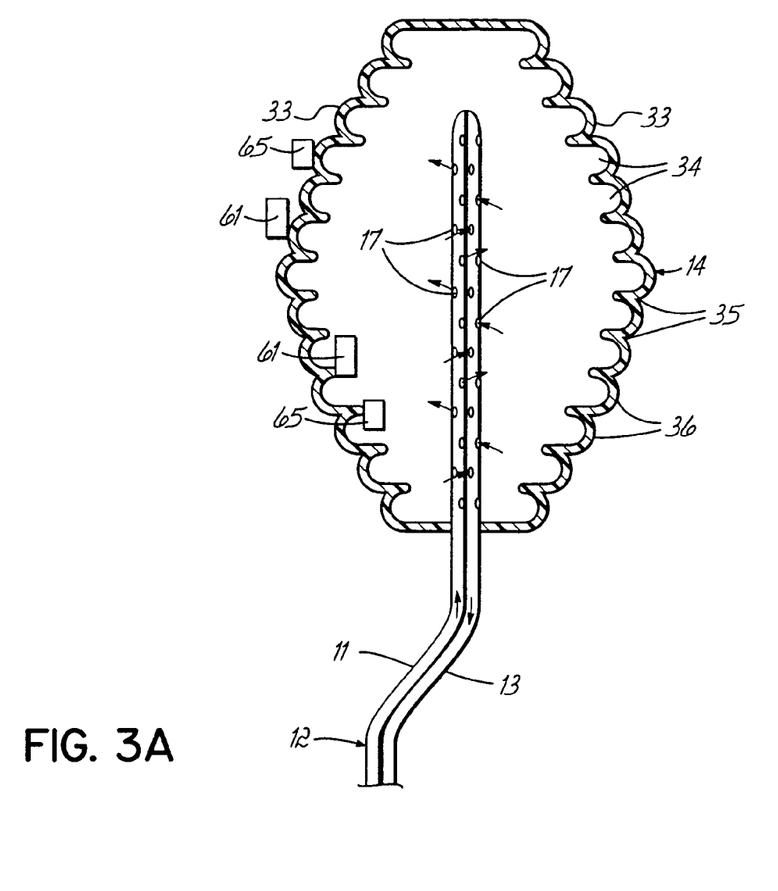
FIG. 3A is a side view, in partial cross-section of a "dry" embodiment of a bulb of FIG. 1.

Referring now to FIG. 2 and FIG. 3A, the head structure in the form of a bulb 14 is shown inserted into the rectal cavity 30 of a patient body 29. Within the rectal cavity 30, the bulb 14 of this embodiment has contact surfaces 36 which will contact the rectal mucosal membrane 32 when the bulb has been inserted into the rectal cavity 30. The contact surface is operable to transfer energy between the fluid and the tissue, and therefore, the head structure is operable for transferring the energy between the fluid and the contact surface. Preferably, the bulb has an effective diameter such that the contact surface or surfaces 36 are in positive contact with the mucosal membrane 32 of the rectal cavity 30. In accordance with one aspect of the invention, the system 10 is used in conjunction with intraabdominal pressure to reverse the flow of blood through Batson's plexus and directly cool or warm the spinal structures 33 with blood that is cooled or warmed by the cooling head structure bulb 14 placed within the rectal cavity 30.

In accordance with one embodiment of the inventive method, the bulb 14 is positioned in the proximal two-thirds (⅔) of the rectal cavity 30 illustrated by reference numeral 31 in FIG. 2. This proximal two-thirds of the rectal cavity is often referred to as the ampulla 31 and is also generally less sensitive than the area directly proximate the anus 28. Therefore, the body 29 should not seek to expel the bulb 14 when placed within the ampulla 31, and the anal region will adapt to the delivery tube 12. A distinct advantage in locating the bulb 14 in the ampulla 31 is that the ampulla is generally drained by the middle and inferior rectal veins (not shown), which return venous blood to the inferior vena cava (not shown). In accordance with the principles of the invention, the blood draining the ampulla 31 is cooled or warmed and delivered by retrograde flow to the spinal structures 33 via Batson's valveless venous plexus. This is accomplished by increasing intraabdominal pressure by an amount high enough to reverse blood flow through this plexus. The intraabdominal pressure may be applied such as by using a velcro lumbar support, an abdominal restraint or binder, or any other medically suitable method for creating increased intraabdominal pressure. Pressure increases in the range of approximately 30-90 mm Hg are generally sufficient although factors such as the body habitus and idiosyncratic factors will influence the required pressures needed to reverse the flow through Batson's plexus. Upon the reversal of pelvic, sacral, and lumbar venous flow, the normal flow of blood that occurs from the spinal column toward the heart is reversed, such that blood flow occurs back into the spinal area. Therefore, using Batson's plexus reverse blood flow with the system 10 in accordance with the principles of the present invention, fluids can cool or warm the blood draining the rectal mucosal membranes 32 and more directly, effectively, and efficiently cool or warm the spinal cord. In one embodiment, cooling to induce hypothermia is desired. Therefore, the embodiments are described herein below with respect to the cooling function for illustrative, not limiting purposes.

FIG. 3A illustrates a side view, in partial cross-section, of one embodiment of a cooling head structure in the form of a bulb 14 which has a generally beehive-shaped cross-section with walls 33 that form outpocketings 34 which define elongated contact surfaces 36 for contacting the mucosal membrane 32 (see FIG. 2). The unique shape of the cooling bulb contact surface 36 having alternating outpocketings 34 and troughs 35 insures positive contact against the mucosal membrane 32 of the rectal cavity 30. This positive contact provides efficient transfer of caloric energy between the rectal mucosal membrane 32 and tissue and the cooling bulb 14 and the fluid therein, and further serves to hold the cooling bulb 14 in place within the rectal cavity 30. Furthermore, the outpocketings 34 of the cooling bulb 14 are dimensioned in depth such that the contact surfaces 36 make positive contact with the rectal mucosal membrane 32 without penetrating or otherwise tearing the delicate lining of the membrane 32.

The delivery tube 12 of this embodiment is made up of an inflow lumen 11 and an outflow lumen 13 that may have multiple holes or openings 17 formed therein. As cooling fluid exits the holes 17 in the inflow lumen 11 of the delivery tube 12, it is directed radially outwardly to the contact surface 36 of the cooling bulb 14. Preferably, there is a sufficient flow of fluid to produce good contact on the inside of the walls 33 for proper cooling and to keep the contact surfaces against the membrane 32. The material of the bulb 14 is operable to provide caloric energy transfer between the fluid and the contact surface 36 through the walls 33. The bulb 14 in this "dry" embodiment is operable to direct the fluid to contact surfaces 36. Heat exchange occurs at the walls 33 and specifically at the contact surfaces 36. Fluid is returned through holes 17 to the outflow lumen 13 of the delivery tube 12, and thereafter exits the rectal cavity. The inflow and outflow of fluid cools or warms the bulb 14 and cools or warms the blood of the rectal tissue.

Figure 3B:
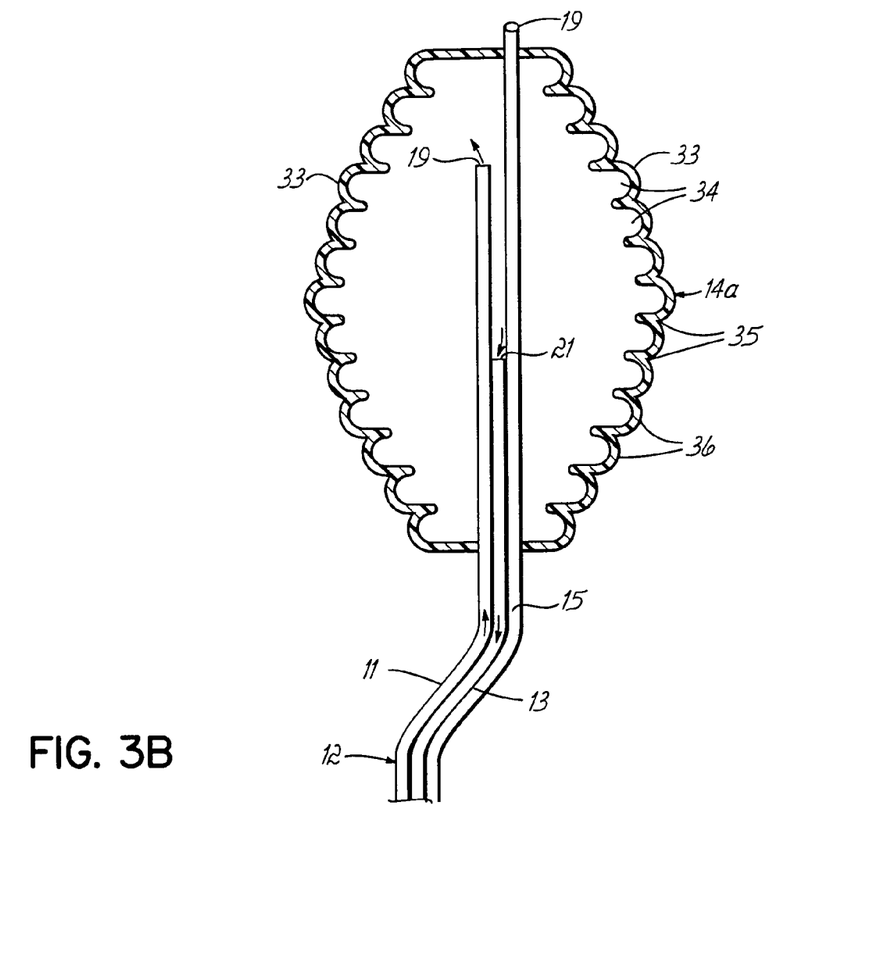
FIG. 3B is a side view, in partial cross-section, of another "dry" embodiment of a bulb.

FIG. 3B illustrates a side view, in partial cross-section, of another "dry" embodiment of the cooling bulb 14a wherein the inflow lumen 11 and the outflow lumen 13 of the delivery tube 12 are not perforated with openings 17. Rather, the inflow lumen 11 and outflow lumen 13 have open terminal ends 19, 21 (shown as staggered) to allow passage of the cooling fluid into and out of the cooling bulb 14a. Cooling fluid exits the outlet or opening 19 of the end of the inflow lumen 11 and is directed radially outwardly to the contact surfaces 36 of the cooling bulb 14a. The fluid that is then returned to an outlet in the end 21 of the outflow lumen 13 and thereafter exits the rectal cavity. The circulating flow maintains the desired temperature of the head structure as it cools/warms the tissue.

FIG. 3B also illustrates an alternative feature of the invention that might be incorporated into any of the "dry" embodiments of the invention, including the embodiments illustrated in FIGS. 3A, 3B, 3C and 4A, for example. The feature is illustrated with respect to FIG. 3B, but is not limited to that embodiment. Referring to FIG. 3B, the delivery tube 12 further comprises an additional lumen 15, which extends through or around the head structure for introducing a substance. The head structure is configured to dispense a substance proximate to the rectal tissue contacted by the head structure. For example, the head structure might dispense a vasodilator. Such a vasodilator or other suitable composition may be utilized to dilate the veins associated with the ampulla 31 to further improve the Batson's plexus cooling or warming effect. In FIG. 3B, lumen 15 is shown to extend through the bulb 14a and terminate in an opening 19 at an end of the bulb. Alternatively, the lumen 15 might terminate elsewhere outside of and proximate to the cooling/warming head structure. Also, rather than having a single outlet 19, the lumen may be perforated with openings, such as those illustrated in FIGS. 3A and 3C. Therefore, the head structure might be configured in various different ways for introducing a vasodilator or other suitable composition for improving the operation of the system in cooling or warming portions of the body.

Figure 3C:
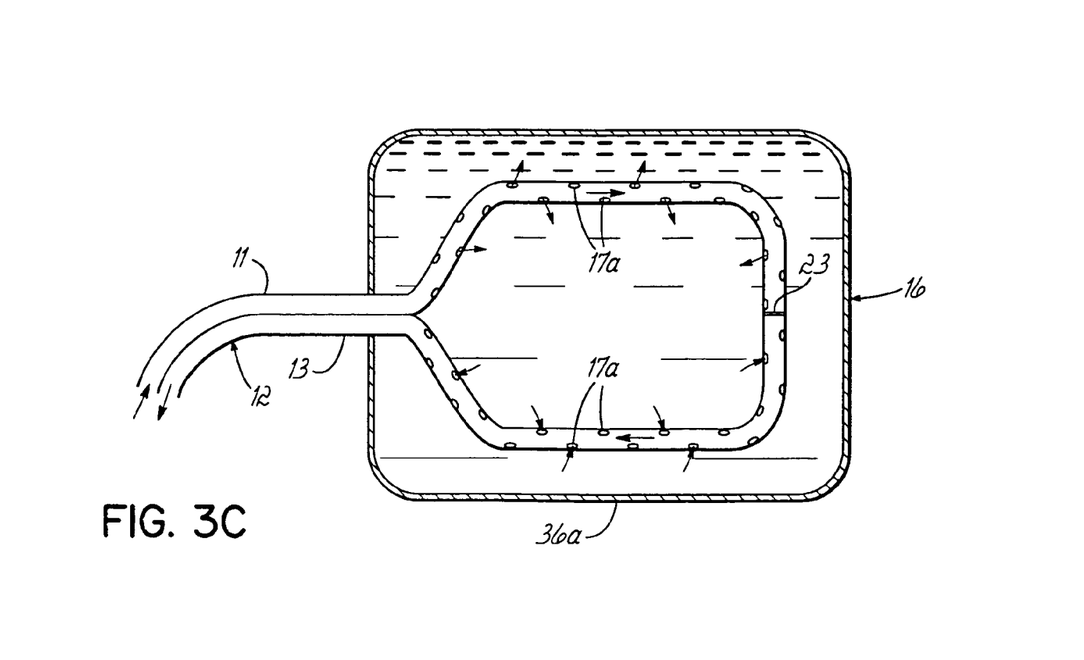
FIG. 3C is a side view, in partial cross-section, of a flexible bag configuration of a head structure of the invention.

FIG. 3C illustrates a side view in partial cross-section of another "dry" embodiment of the cooling bulb, which is generally configured as a flexible bag 16. This flexible bag 16 receives the delivery tube 12. The delivery tube 12 in this embodiment comprises an inflow lumen 11 and an outflow lumen 13 that may be joined together at wall 23 to form a loop. When the delivery tube enters the bag 16, holes 17a operate to deliver the cooling fluid into the cooling head structure bag 16 to fill it. Holes 17a also return fluid to tube 13 to provide through circulation. Alternatively, the delivery tube 12 depicted in FIG. 3B can be used as well. The cooling head structure bag 16 is flexible and its shape is able to expand and conform to the shape of the rectal cavity when cooling fluid is delivered, so that the contact surface 36a of the bag 16 makes extensive contact with the rectal mucosal membrane. In this embodiment, the bag 16 expands in proportion to the inflow rate of the cooling fluid. Therefore, as the flow rate of the cooling fluid is increased, the internal pressure and size of the bag 16 also increases. There is a limit to the size of the expanding bag 16 so that the rectal cavity 30 does not reflexively expel the bag 16. A pump device 38 preferably delivers and retrieves the cooling fluid in this embodiment (see FIG. 1).

Although the system's supply of cooling fluid can be delivered either through an IV drip bag 37 or through a pump 38 or through some other suitable method, it may be desirable to deliver the cooling fluid via a pump apparatus 38 in order to have control over both the inflow rate of the cooling fluid and the pressure generated within the cooling head structure bulb 14. Where the bulb is in the form of an expanding bag 16 (FIG. 3C), pressure is necessary in order to inflate the bag 16 and allow it to conform to the shape of the rectal cavity 30. With this expandable bag embodiment, the pressure generated within the cooling head structure bag 16 is proportional to the inflow rate of the cooling fluid, so that the inflow rate of the cooling fluid should be carefully monitored to avoid overpressurizing the cooling head structure bulb. In the beehive-shaped bulb embodiment (FIG. 1), however, the cooling head structure bulb 14 has flexible pockets 34 that are pliable and conform more easily to the shape of the rectal cavity 30, such that the inflow rate of the cooling fluid might be increased with no appreciable increase in pressure within the cooling head structure bulb 14.

In accordance with another aspect of the present invention, various monitors are utilized to provide temperature and pressure feedback to a caregiver or operator who is utilizing the system. Referring to FIG. 3A, a temperature sensor 61, such as a thermocouple, may be incorporated on the inside of the head structure to monitor the temperature of the cooling or warming fluid. Based on that temperature, the fluid might be further cooled or further heated to achieve the desired result. Similarly, a temperature sensor 61 might be incorporated externally of the head structure, as illustrated in FIG. 3A, for providing temperature feedback with respect to the membrane 32, which is being cooled.

As noted above, pressure monitoring may also be desirable. Therefore, the system might incorporate a pressure sensor 65 which may be incorporated internally or externally of the head structure, as illustrated in FIG. 3A. The pressure sensor 65 monitors the fluid pressure created internally of the head structure, or proximate the mucous membrane, so that the pressure might be controlled to yield desirable results and to prevent tissue damage. Although the temperature sensor 61 and pressure sensor 65 are indicated in the "dry" version of the head structure, as illustrated in FIG. 3A, such sensors might be incorporated in other embodiments of a "dry" head structure, and might also be incorporated into a "wet" embodiment of the head structure to provide desirable temperature and pressure monitoring.

The ampulla 31 and the rectum proper 39 are generally not as sensitive to the placement of a foreign body as is the end of the rectal cavity 30 proximate the anal region or anus 28. Therefore, the body 29 will generally sense only the thin delivery tube 12 in the anal region 28, and will adapt to the minor discomfort of the tube 12 without seeking to expel the cooling bulb 14 (FIG. 2). Since the cooling bulb 14 is lightweight and will preferably remain generally static within the rectal cavity 30 once it has expanded, the bulb has minimal effects on the nerve endings in the rectal cavity 30. Therefore, the body 29 preferably does not sense the cooling bulb 14 as a stool and will not react or respond to expel it from the rectal cavity 30. However, should a bowel movement occur, the stool would push the cooling head structure bulb 14 out of the rectal cavity 30 as desired. Bowel preparations, such as those used with precolonoscopy procedures, would preclude this from occurring. The material utilized to form the head structure should preferably not foster the growth of microflora. While the cooling system 10 of the present invention utilizes a head structure which is preferably configured for remaining unobtrusively within the rectal cavity 30, it may be useful to precede the insertion of the head structure with an anesthetic around the anus 28 and in the rectal cavity 30 to prevent immediate expulsion of the head structure as a foreign body. Furthermore, the head structure is preferably coated with an appropriate lubricant or oil such as paraffin oil or silicon oil to facilitate easy insertion of the head structure. The cooling system of the present invention will be generally inexpensive to manufacture and to utilize.

Figure 4A:
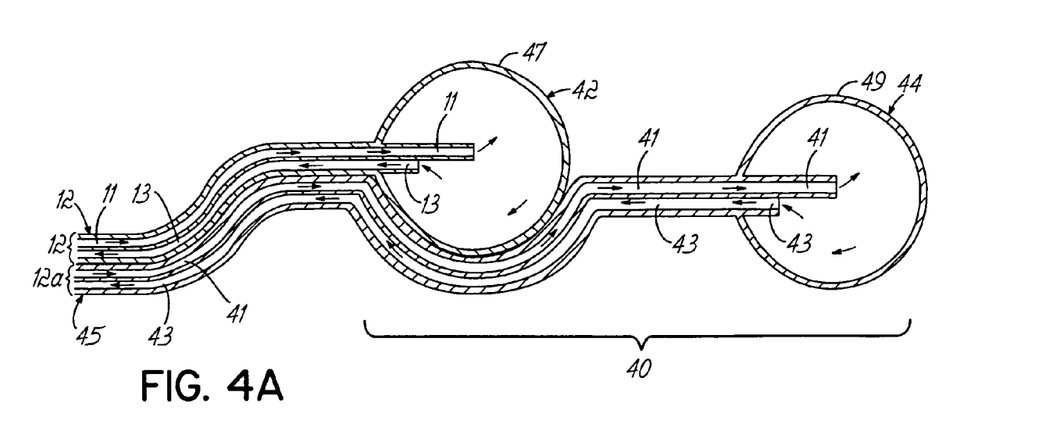
FIG. 4A is a side view in partial cross-section, of a tandem bulb configuration of a "dry" embodiment of the head structure.

As illustrated in FIG. 4A in accordance with another "dry" embodiment of the invention, the head structure 40 has tandem bulbs 42, 44 and is to have a warm or non-cooled portion, such as a warm or non-cooled distal bulb 44, positioned in tandem with a cooler portion, such as a cooled proximal bulb 42. In this embodiment having a tandem bulb head structure 40, the proximal or cold bulb 42 receives the cooling fluid while the distal or warm bulb 44 remains warm or is simply non-cooled or at normal body temperature. That is, the distal bulb 44 may be actively warmed to body temperature or above for warming as discussed below, or it may simply not be actively cooled like the proximal bulb 42. FIG. 4A illustrates another delivery tube 12a with an inflow lumen, or incourse lumen 41, and an outflow lumen, or outcourse lumen 43, which delivers the fluid to the distal bulb 44. The incourse lumen 41 and outcourse lumen 43 make up the delivery or transfer tube 12a which may be similar to the delivery tube 12 which delivers fluid to the proximal cooled bulb 42. The lumens might all be configured as a single structure or separately. In an alternative embodiment, the lumens 11, 13, 41, 43 might not simply terminate in the bulbs, but may have openings like openings 17, 17a illustrated in FIGS. 3A, 3C or other appropriate forms for circulating fluid.

Figure 4B:
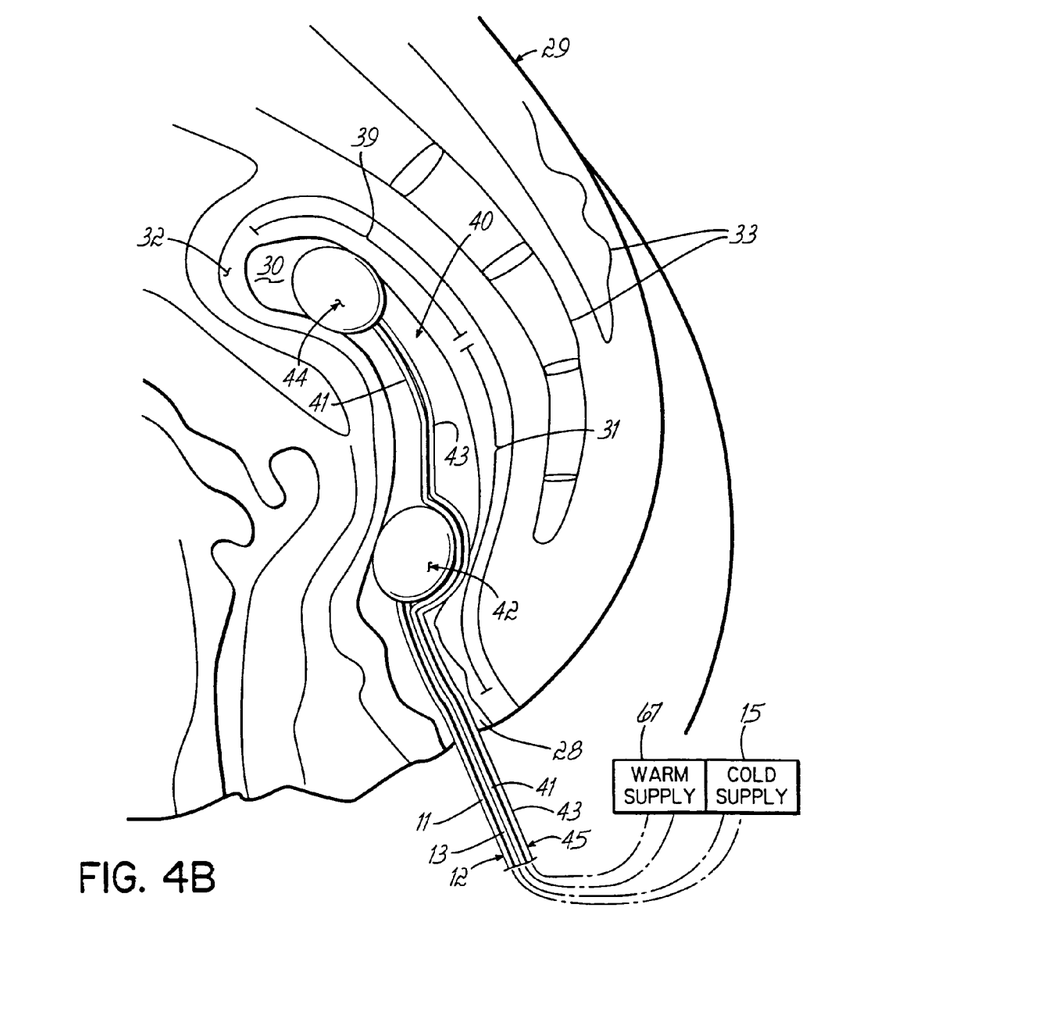
FIG. 4B is a side view, in partial cross-section, of a patient body illustrating one embodiment of the system with the head structure of FIG. 4A used within the rectal cavity of the body.

FIG. 4B illustrates the embodiment illustrated in FIG. 4A inserted into the rectal cavity 30 of the patient body 29. In this embodiment, the proximal bulb 42 is positioned in the proximal two-thirds 31 of the rectum, or ampulla. The inferior and middle rectal veins drain the ampulla 31. When intraabdominal pressure is applied, blood draining this part 31 of the rectal cavity 30, having been warmed or cooled, flows retrograde through Batson's plexus. This retrograde flow of blood through Batson's plexus acts to directly cool or warm the central nervous system structures 33. In this embodiment, the distal bulb 44 is positioned in the distal or most internal one-third (⅓) of the rectal cavity 30, as illustrated by reference numeral 39 in FIG. 4B. This section is referred to as the rectum proper 39. Preferably, a bulb has an effective diameter such that the contact surfaces 47, 49 are in positive contact with the mucosal membrane 32 of the portion of the rectal cavity 30 with which it makes contact. Therefore, the distal bulb of the tandem bulb embodiment may have a larger diameter than the proximal bulb, since the internal circumference of the rectal cavity is larger in the rectum proper 39 than it is in the ampulla 31.

The bulb 44 may be used in order to keep the remaining organs of the patient body 29 warm or unwarmed during central nervous system cooling or warming. One of the drawbacks of the prior art is that cooling of the entire body is required in order to cool the target organ, the central nervous system. With the system and method of the present invention, selective cooling of the central nervous system can take place even while the rest of the body is either not cooled or actively warmed.

In one embodiment, the warm distal bulb 44 may be actively warmed. As illustrated in FIG. 4B, the system of this embodiment might further include a supply 67 of warming fluid in addition to a supply 15 of cooling fluid. This warming fluid is preferably warm water or warm saline solution, but can be any fluid capable of transferring caloric energy between the rectal mucosal membrane 32 and the head structure or bulb. Warming fluid is used to transfer heat to the rectal mucosal membrane 32 in the rectum proper 39 if the ampulla is cooled, for example. The rectum proper 39 is perfused and drained by the superior rectal vein (not shown), which drains into the portal vein (not shown), and subsequently into the liver (not shown). The venous blood feeding the superior rectal vein does not come from the vertebral venous (Batson's) plexus. Therefore, when intraabdominal pressure is applied, this warmed blood does not flow retrograde to the central nervous system structures 33 through Batson's plexus, but rather is available to warm the rest of the body 29. In this embodiment, therefore, the actively warmed distal bulb 44 is operable to allow the rectal mucosal membrane 32 of the rectum proper 39 to absorb caloric energy and warm the rest of the patient's body 29, while the actively cooled proximal bulb 42 is operable to absorb caloric energy from the rectal mucosal membrane 32 of the ampulla 31 to cool the patient's central nervous system structures 33. In this manner, the central nervous system is selectively cooled. Alternatively, both of the bulbs 42, 44 might be warmed to warm or re-warm the patient in accordance with the present invention.

Figure 5A:
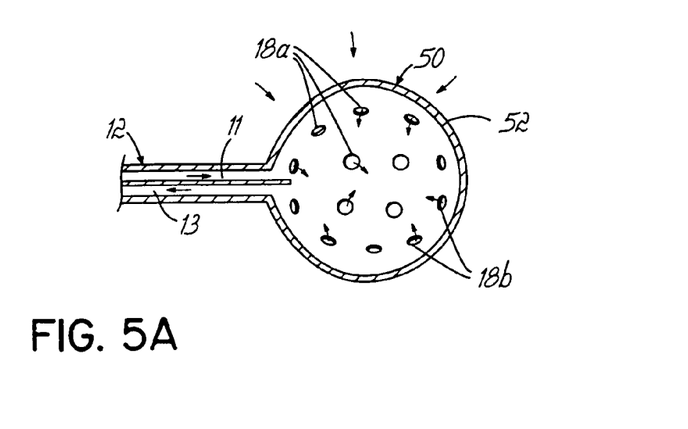
FIG. 5A is a side view, in partial cross-section, of a "wet" embodiment of the head structure.

FIG. 5A illustrates a side view and partial cross-section of another embodiment of the system wherein the fluid exits the head structure. This "wet" embodiment of the head structure in the form of a bulb 50 has openings or apertures 18a, 18b through the contact surface 52 which have the function of permitting both inflow and outflow of fluid from the bulb 50. These apertures 18 are in fluid communication with the inside of the bulb such that the fluid is able to escape the bulb and directly bathe and cool or warm the rectal mucosal membrane proximate the bulb. In this embodiment, the fluid is first delivered to the bulb 50 via the inflow lumen 11 of the delivery tube 12. The cooling fluid exits the cooling head structure bulb 50 through the apertures 18a and bathes the rectal mucosa, such as to cool it. The fluid is then retrieved or collected through apertures 18b and delivered to the outflow lumen 13 of the delivery tube 12 and out of the patient. A pump device preferably delivers and retrieves the cooling fluid in this embodiment. In the bulb, the apertures 18a are preferably segregated from apertures 18b so that the delivery of the fluid and the collection of the used fluid are independent functions. That is, segregated volumes may exist in the bulb that are linked separately to the lumens 11, 13.

Multiple head structures like those shown in FIGS. 1, 2, 3A, 3B, 3C, 4A, 4B, 5A, 5B, 7A, 7B and elsewhere described herein might be used in accordance with the principles of the present invention. For example, multiple such head structures might be used to cool or warm a body and might be used simultaneously to speed the process. For example, two or more bulbs 14 or 50 might be used in a body. Therefore, the invention is not limited to the number of head structures used.

Figure 5B:
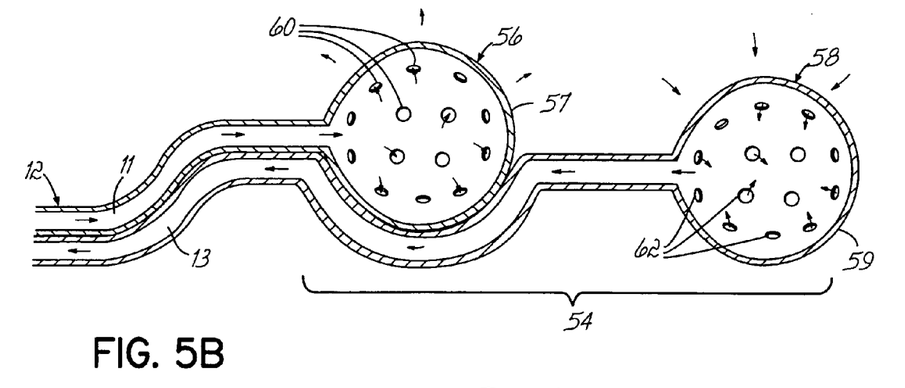
FIG. 5B is a side view, in partial cross-section of a tandem bulb configuration of a "wet" embodiment of the head structure of the invention.

FIG. 5B illustrates a side view and partial cross-section of yet another "wet" embodiment of the system wherein the cooling head structure 54 is configured having a proximal bulb 56 and a distal bulb 58 positioned in tandem to each other. In this embodiment, the multiple bulbs separate the dispersal and collection of fluid. As noted above, the distal bulb 58 of a tandem bulb embodiment might have a larger diameter than the proximal bulb 56, since the internal circumference of the rectal cavity is larger in the rectum proper 39 than it is in the ampulla 31. This ensures direct contact of the respective contact surfaces 57, 59 with the rectal mucosal membrane 32. In this embodiment, there are outlet apertures 60 formed through the contact surface 57 of the proximal bulb 56 and inlet apertures 62 formed through the contact surface of the distal bulb 58. These apertures 60 and 62 are in fluid communication with the rectal cavity such that the cooling fluid is able to directly bathe and cool or warm the rectal mucosal membrane. The fluid is first delivered to the proximal bulb 56 via the inflow lumen 11 of the delivery tube 12. The fluid exits the outlet apertures 60 of the proximal bulb 56 and bathes the rectal mucosal membrane. The used fluid is then retrieved through the inlet apertures 62 of the distal bulb 58 and delivered to the outflow lumen 13 of the delivery tube 12 and out of the patient. A pump device preferably delivers and retrieves the cooling fluid in this embodiment.

Figure 6:
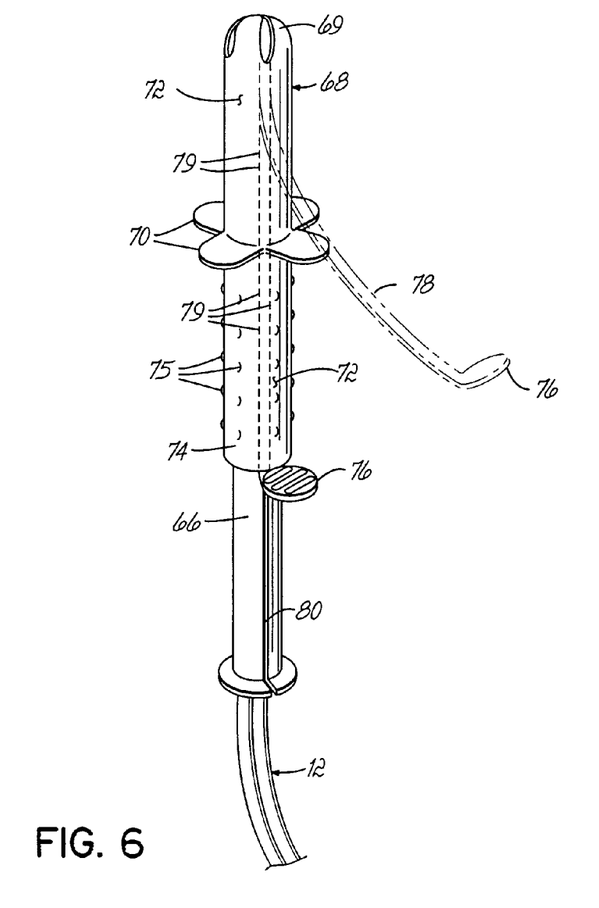
FIG. 6 is a perspective view of an applicator sheath and plunger of the invention for inserting a head structure into a body cavity.

In the open "wet" version of the embodiment, the fluid may be saline or water, or alternatively, may be a fluid, which is generally not absorbable in the bloodstream of the patient. A nonabsorbable fluid would assure that the patient does not develop problems associated with increased fluid load or electrolyte imbalance. In another embodiment, the fluid might be at least partially absorbable into the bloodstream of the patient. In still another embodiment, the fluid may include an absorbable substance, which is absorbed into the bloodstream. For example, the fluid might include an absorbable vasodilator medication that can act to increase the blood flow to and from the rectal membrane, thereby increasing the amount of blood that is actively cooled or warmed in the system. Referring now to FIG. 6, the cooling head structure (not shown, which can be "dry" (FIGS. 1-4) or "wet" (FIGS. 5, 7)), is compressed prior to insertion by being coupled at one end to a plunger 66 for slidably moving the head structure within an applicator sheath 68. The applicator sheath 68 is elongated and contains the head structure in a compressed state while the applicator is inserted into the rectal cavity. Sheath 68 has a split end 69, which spreads apart and allows the head structure to be pushed therethrough when plunger 66 is moved with respect to applicator sheath 68. Once the head structure has been inserted into the rectal cavity, the sheath 68 and plunger 66 can be removed as described further herein below. The sheath 68 preferably includes peripheral tabs 70 which set the insertion depth of the top section 72 of sheath 68. The top section 72 is smooth for easy insertion into the rectal cavity through the anus 28. The top section 72 might be lubricated with a suitable lubricant for easy insertion into the rectal cavity 30. The bottom section 74 of the applicator sheath 68 includes a plurality of dimples 75 to provide a gripping surface for fingers when the plunger 66 is pushed into the sheath 68 to eject the head structure.

As illustrated in FIG. 6, the applicator sheath 68 and plunger 66 of the invention are preferably dimensioned so that the head structure may be properly located within the rectum. The sheath 68 may be formed of polyethylene, while the plunger 66 may be an impact-resistant polystyrene, for example. Applicator sheath 68 includes a pull-tab 76 connected to a longitudinal tear-away strip 78 formed by perforations 79 along the length of the sheath 68. The pull-tab is pulled away from sheath 68 as illustrated in phantom in FIG. 5 to tear away the strip 78. When the strip 78 is torn away, a longitudinal slit is left on the sheath 68 to allow for easy removal of the sheath 68 from the plunger 66 and delivery tube 12. The plunger 66 also has a preformed longitudinal slit 80 that allows the plunger to be spread marginally along the slit so that the plunger 66 may also be removed from around the delivery tube 12 once the head structure has been inserted into the rectal cavity 30. The sheath 68 and plunger 66 can then be properly disposed of, leaving only the cooling head structure bulb and a portion of the delivery tube 12 within the rectal cavity 30.

In one embodiment of the invention, the head structure is generally resilient and/or flexible, and will expand to the desired shape and size when the sheath 68 is withdrawn. Alternatively, the head structure, such as bulb 14 (FIG. 1), or 16 (FIG. 3C) might have to be actively expanded such as with a pump system. When the sheath 68 is withdrawn, such as by pressing the bulb 14 (FIG. 1) out of the split end 69 of the sheath 68 by pushing plunger 66 into the sheath, the bulb 14 expands to its desired shape, or may be expanded by pumping.

Referring again to FIG. 1, a disposal package 26 is slidably coupled to the delivery tube 12 by a rubber or foam gasket seal 27. When the bulb 14 has been used and withdrawn from the rectal cavity 30, the disposal package 26 may be slid up along the length of delivery tube 12 to thereby receive the bulb 14. The seal 27 is used to wipe the delivery tube 12 clean prior to disposal within package 26. The tube 12 then preferably detaches from the head structure or bulb 14 and is placed in the disposal package 26. An adhesive strip 25 on a seal flap 23 of the disposal package 26 seals the flap 23 against the package 26 for safe disposal of the used bulb 14 and delivery tube 12.

Figure 7A:
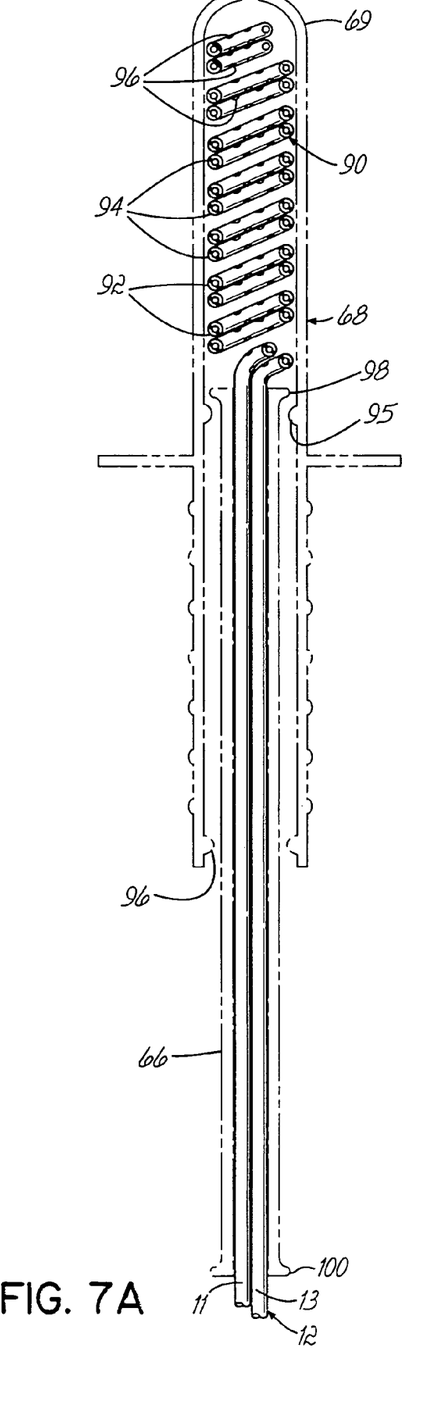
FIG. 7A is a cross-sectional view of an alternative embodiment of the head structure of the invention shown compressed within the applicator sheath.
Figure 7B:
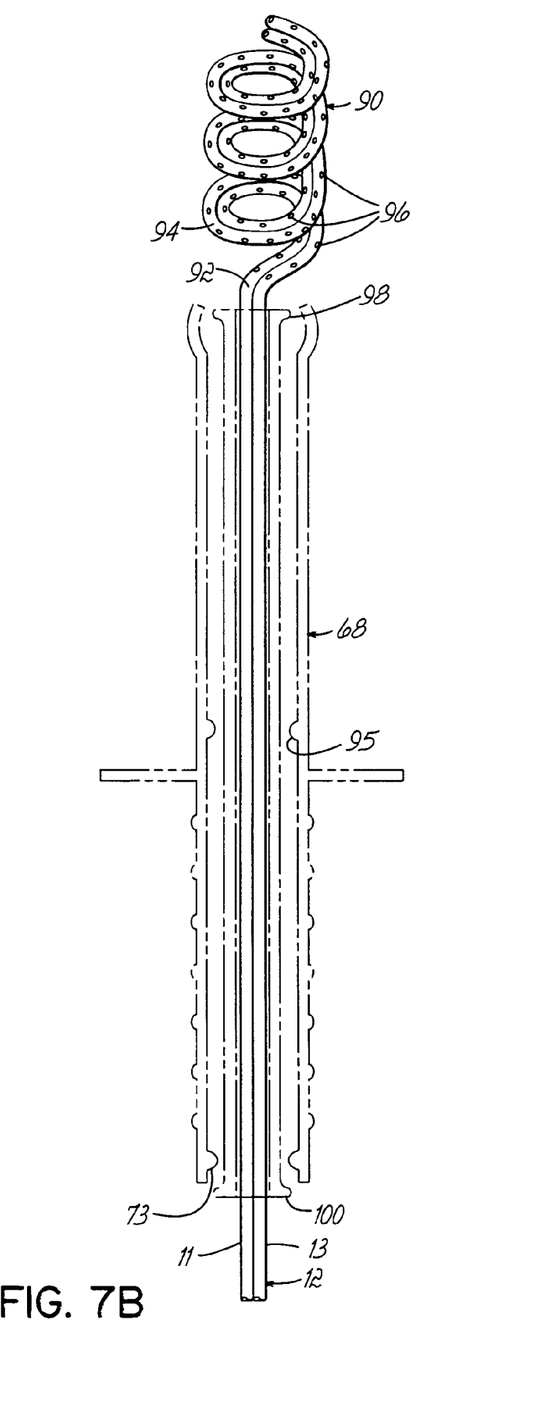
FIG. 7B is a side cross-sectional view of the head structure of FIG. 7A with the sheath retracted and the bulb expanded.

FIGS. 7A and 7B illustrate a further alternative embodiment of a head structure of the present invention. As illustrated, the head structure includes a pigtailed or helical coiled or helix element 90. The element 90 includes an inflow coil 92 for dispensing fluid and an outflow coil 94 for withdrawing the fluid. The coils 90, 92 are wound together in an elongated shape and include a plurality of fluid-dispensing and withdrawing apertures 96 formed therein. Therefore, the embodiment is a "wet" embodiment. When the coiled element 90 is surrounded by a sheath 68, it is held in a compressed state for application into the rectal cavity (see FIG. 7A). Upon projecting the coiled element 90 out of the end of sheath 68 with the plunger 66, the coiled element 90 then expands in diameter to form a generally elongated cylindrical structure to contact the rectal mucosal membrane 32. The sheath 68 has an upper detent 95 that encircles the plunger 66 and a lower detent 96 that also encircles the plunger. The detents 95, 96 keep the plunger 66 aligned and also act against end ridges 98, 100 on the plunger to contain the plunger 66 in the sheath 48. The outer surfaces of the coils 92, 94 of the coiled element 90 provide contact surfaces and fluid is dispensed through the delivery tube 12 and out of the coil 92 through the apertures 72, and is then drawn back in by coil 94. The coiled element 90 is appropriately coupled to the cooling fluid delivery tube 12.

The coiled element 90 in an expanded state is preferably configured to fit snugly within the rectal cavity 30 of a patient and is preferably made of a lightweight material that is sufficiently strong enough to maintain its expanded shape within the body cavity. Preferably, however, the coils 92, 94 are not too rigid, in order to avoid abrading the delicate rectal mucosal membrane 32. The coiled element 90 operates in accordance with the principles of the invention as discussed herein above.

Should it be undesirable to use the sheath and plunger system illustrated in one embodiment of invention, the head structure might be positioned within the body cavity by a caregiver, such as by using a gloved finger. To aid in the insertion of the head structure and positioning at the proper location, the delivery tube 12 preferably includes a depth marker such as a rib or ring 57 (FIG. 1) on the delivery tube for indicating to the user that the cooling head structure has been located at the proper position within the rectal cavity (FIG. 1). Alternatively, a section of the delivery tube might be color coated. For example, the section of tube between the marker 57 and cooling head structure might be a different color than the remaining section of the tube from the marker 57 back to the cooling fluid supply. Furthermore, the tubing 12 may be impregnated with radiopaque marks along its length.

Selective central nervous system cooling with minimal systemic cooling may be achieved with the inventive system and method. Thus, the invention provides a number of distinct advantages. Cooled blood is directly delivered into the vertebral structures instead of systemically throughout the body. Furthermore, the cooled blood is delivered to the vertebral structures before significant mixing or dilution with warmer systemic blood occurs. Side effects such as shivering and "overshoot" cooling are therefore reduced. Cooling fluid dispensed through the head structure acts to cool the rectal mucosal membrane. Since the cooling system of the invention is utilized within a formed body cavity, it is non-invasive and generally non-painful. Since it is non-invasive, use of the system of the invention is not accompanied by the various drawbacks experienced with more invasive techniques. During operation of the cooling system, it is easy to initiate the administration of cooling fluid simply by providing cooling fluid flow through the delivery tube and into the cooling head structure bulb. Similarly, stopping the cooling fluid flow will terminate the administration whereupon it can simply be reinitiated by again beginning the flow through the delivery tube. Warming or re-warming may also be similarly handled.

In one embodiment, the cooling head structure bulb, either "dry" or "wet," may be dimensioned approximately 2.5 cm in length. The cooling head structure bulb is further pliable enough to deform to a compressed state and a smaller effective diameter when it is removed from the body cavity, such as by being pulled through the anal sphincter (not shown) of the anus 28. Preferably, the cooling head structure bulb is colored a special color, such as a dark yellow, to reduce the soiled appearance of the cooling head structure bulb when it is removed. The elements of the cooling system should preferably be able to withstand gamma radiation for the purpose of pre-use sterilization. Furthermore, the materials are preferably safe to use in the presence of medical diagnostic systems such as magnetic resonance imaging (MRI), X-ray, or computerized tomography (CT) scan.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. A system for cooling or warming a portion of a body of a patient, comprising:
    a supply of fluid;
    a head structure configured to receive the fluid;
    a delivery tube coupled between the supply and head structure for delivering fluid to the head structure;
    the head structure configured to be positioned within the rectal cavity of a patient and further including a proximal bulb and a distal bulb, the proximal bulb having a plurality of outflow apertures operable to disperse the fluid to contact the rectal tissue in the cavity for transferring caloric energy between the rectal tissue and the fluid; and
    means for reversing the vertebral venous flow of blood through Batson's plexus to supply blood, affected by the temperature of the fluid, to the vertebral structures.

2. The device of claim 1, wherein the fluid is generally not absorbable into the bloodstream of a patient through the rectal tissue.

3. The system of claim 1, wherein the fluid is at least partially absorbable into the bloodstream of a patient through the rectal tissue.

4. The system of claim 3, wherein the fluid further comprises an absorbable vasodilator composition.

5. The system of claim 1, further comprising a supply of cooling fluid coupled to the proximal bulb to be dispersed by the proximal bulb.

6. The system of claim 1, further comprising a supply of warming fluid coupled to the proximal bulb to be dispersed by the proximal bulb.

7. The system of claim 1, wherein at least one of the bulbs is configured for dispensing a substance proximate to the rectal tissue contacted by the bulb.

8. The system of claim 1, wherein the distal bulb comprises a plurality of inflow apertures for capturing dispersed fluid after it has contacted the rectal tissue.

9. The system of claim 1, the delivery tube further comprising an inflow lumen and an outflow lumen, the inflow lumen operable to deliver the fluid to the head structure, the outflow lumen operable to remove the fluid from the head structure.

10. The system of claim 1, wherein the means for reversing vertebral venous blood flow through Batson's plexus is selected from the group consisting of a lumbar support, an abdominal restraint, and an abdominal binder.

11. The system of claim 1, wherein the proximal bulb is configured for being positioned within the portion of the rectum generally drained by at least one of the middle and inferior rectal veins.

12. The system of claim 1, wherein the distal bulb is configured for being positioned at least partially within a portion of the rectal cavity generally drained by the superior rectal vein.

13. A system for cooling or warming a portion of a body of a patient, comprising:
    a supply of fluid;
    a head structure configured to receive the fluid;
    a delivery tube coupled between the supply and head structure for delivering fluid to the head structure;
    the head structure configured to be positioned within the rectal cavity of a patient and operable to disperse the fluid to contact the rectal tissue in the cavity for transferring caloric energy between the rectal tissue and the fluid, the head structure further including a plurality of inflow apertures formed therein and operable for capturing dispersed fluid after it has contacted the rectal tissue; and
    means for reversing the vertebral venous flow of blood through Batson's plexus to supply blood, affected by the temperature of the fluid, to the vertebral structures.

14. The system of claim 13, wherein the fluid is at least partially absorbable into the bloodstream of a patient through the rectal tissue.

15. The system of claim 14, wherein the fluid further comprises an absorbable vasodilator composition.

16. The system of claim 13, wherein the head structure further comprises a plurality of outflow apertures for dispersing the fluid.

17. The system of claim 13, the delivery tube further comprising an inflow lumen and an outflow lumen, the inflow lumen operable to deliver the fluid to the head structure, the outflow lumen operable to remove the fluid from the head structure.

18. The system of claim 13, wherein the means for reversing vertebral venous blood flow through Batson's plexus is selected from the group consisting of a lumbar support, an abdominal restraint, and an abdominal binder.

* * * * *